(12) United States Patent
Davies et al.

(10) Patent No.: US 6,943,035 B1
(45) Date of Patent: Sep. 13, 2005

(54) LIQUID DISPENSING APPARATUS AND METHOD

(75) Inventors: Douglas Davies, Bransgore (GB); James Keith Haslam, Blandford Forum (GB); Sarah Katharine Stephens, Bransgore (GB)

(73) Assignee: Genetix Limited, Dorset (GB)

( * ) Notice: Subject to any disclaimer, the term of this patent is extended or adjusted under 35 U.S.C. 154(b) by 0 days.

(21) Appl. No.: 09/573,998

(22) Filed: May 19, 2000

(51) Int. Cl.$^7$ ................................................ G01N 1/10
(52) U.S. Cl. ...................... 436/180; 436/174; 436/177; 436/179; 422/99; 422/100; 422/102
(58) Field of Search ................ 436/179, 174, 436/177, 178, 180; 422/61, 58, 99, 100, 102, 101

(56) References Cited

U.S. PATENT DOCUMENTS

| | | | |
|---|---|---|---|
| 3,894,950 A | | 7/1975 | Ayres et al. ................. 210/131 |
| 4,827,780 A | | 5/1989 | Sarrine et al. ............ 73/864.21 |
| 5,281,540 A | * | 1/1994 | Merkh et al. ................ 436/530 |
| 5,578,495 A | * | 11/1996 | Wilks ........................... 436/178 |
| 5,789,251 A | | 8/1998 | Astle ............................ 436/48 |
| 5,916,812 A | * | 6/1999 | Chen et al. .................... 436/18 |
| 5,935,523 A | * | 8/1999 | McCandless et al. ........ 422/100 |
| 5,951,783 A | | 9/1999 | Kontorovich et al. .......... 134/21 |
| 5,972,694 A | | 10/1999 | Mathus .................... 435/288.4 |
| 6,030,582 A | * | 2/2000 | Levy ............................ 422/99 |
| 6,045,755 A | * | 4/2000 | Lebl et al. ..................... 422/65 |
| 6,054,099 A | * | 4/2000 | Levy ............................ 422/102 |
| 6,254,833 B1 | * | 7/2001 | Shumate et al. ............. 422/102 |
| 6,361,744 B1 | * | 3/2002 | Levy ............................ 422/99 |
| 6,534,019 B1 | * | 3/2003 | Inoue ........................... 422/130 |
| 6,551,557 B1 | * | 4/2003 | Rose et al. ................... 422/100 |

FOREIGN PATENT DOCUMENTS

| | | |
|---|---|---|
| WO | 98/36260 | 8/1998 |
| WO | 00/01798 | 1/2000 |

* cited by examiner

*Primary Examiner*—Jill Warden
*Assistant Examiner*—Dwayne K Handy
(74) *Attorney, Agent, or Firm*—Foley & Lardner LLP

(57) ABSTRACT

A multiwell plate for microarraying comprising a self-sealing lower membrane and optionally also a self-sealing upper membrane. Spotting is performed by pushing a pin down through the liquid and then on to pierce the self-sealing lower membrane. A slide having an upper spotting surface is arranged under the well plate. The liquid sample forced through the lower membrane by the pin tip can thus be deposited directly onto the spotting surface. The pin is then withdrawn upwards through the lower membrane, which automatically reseals preventing further loss of liquid. The optional resealable upper membrane also prevents loss of sample liquid by evaporation and spillage. By contrast to the prior art, there is the major advantage that the pin head does not have to traverse between the well plate and slide to collect sample liquid, thus dramatically increasing operational speed for an automated microarraying apparatus employing the multiwell plate. Excellent spot reproducibility is also observed.

19 Claims, 5 Drawing Sheets

LIQUID DISPENSING APPARATUS AND METHOD

BACKGROUND ART

The invention relates to an apparatus for and method of dispensing liquid. More especially, but not exclusively, the invention relates to dispensing liquid from well plates as widely used in the field of chemistry and biotechnology for microarraying and other applications.

Microarraying is a technique in widespread use. Conventional microarraying is based on standard multi-well plates having a 4.5 mm grid and 384 wells. However, larger array sizes of 1536 wells are becoming more widely used, these larger arrays conform to a 2.25 mm grid. Liquid samples are stored in the wells of a well plate. The liquid may be assays or any other biological or chemical sample of interest. To spot the liquid from a well, a pin is dipped in the well to retrieve an amount of the liquid. The pin carrying an amount of the sample liquid is then moved across to a spotting surface of a microscope slide or other suitable surface. A spot of liquid is deposited on the slide by bringing the pin into close proximity, or by physically contacting the tip of the pin, with the slide surface.

FIG. 1A of the accompanying drawings shows schematically a pin 110 conventionally used for spotting. The pin is in the form of a split pin, with liquid 111 being attracted to and carried on the pin by capillary action. The liquid is discharged from the pin onto the spotting surface by lowering or tapping the pin on the spotting surface so that the liquid transfers from the pin tip onto the spotting surface.

FIG. 1B of the accompanying drawings shows schematically a modified split pin design, also used for spotting in the prior art. Split pin 110 incorporates a reservoir 112 and has a blunt end so that liquid 111 extends beyond the pin tip. Liquid can be deposited onto a spotting surface by pressing the blunt end of the pin in contact with the spotting surface or by bringing the pin into very close proximity with the surface such that surface tension causes a drop to be transferred from pin to surface.

These pin designs have in common that they rely on capillary action to gain a reservoir of sample liquid sufficient for many spot depositions. This avoids having to dip into the well for each spot.

Most microarray pins in the prior art float vertically in a common head. They rest in the lowest position by gravity or spring biasing. The head tends to over travel by a small amount and the pins will lift in the head by the over travel.

Regardless of the pin design, spotting is carried out with the following basic steps. The pin is moved to above the well plate. The pin is dipped in a well of the well plate to retrieve some liquid. The pin carrying the liquid is moved over to above the spotting surface. The retrieved liquid is deposited from the pin onto the spotting surface, either with only one spot, or with several spots for a pin that carries a reservoir of sample liquid. The pin is moved back to the well plate to retrieve more liquid for further spotting.

FIGS. 2A to 2C of the accompanying drawings show the basic spotting process. In FIG. 2A, a pin 110 from a pin head 120 is lowered downwards, for example mechanically, to dip it into a well 112 of a well plate 114 and thereby retrieve an amount of liquid sample. In FIG. 2B, the liquid sample is deposited onto a spotting surface. In FIG. 2C, the pin is cleaned in a washing stage 118, typically after many spotting actions (i.e. FIG. 2A to FIG. 2B repeats) prior to commencing spotting with a different liquid sample.

Design effort has been concentrated on speeding up the head transit times so that the time taken between dipping in the well plate and spot deposition on the slide is reduced. As mentioned further above, the pins are also sometimes designed to use capillary action for storing a charge of liquid in the pin sufficient for depositing a number of spots. This also speeds up the spotting procedure by reducing the number of times the head needs to be traversed between the well plate and the slide.

SUMMARY OF THE INVENTION

According to a first aspect of the invention, there is provided a well plate with a self-sealing lower membrane. Spotting is performed by pushing a pin down through the liquid and then on to pierce the self-sealing lower membrane. A spotting surface is arranged under the well plate. The liquid sample forced through the lower membrane by the pin tip can thus be deposited directly onto the spotting surface. The pin is then withdrawn upwards through the lower membrane, which automatically reseals preventing further loss of liquid.

By contrast to the prior art, the pin head does not have to traverse between the well plate and spotting surface to collect sample liquid, thus dramatically increasing operational speed. Moreover, experiments have proved that the spot size obtained by deposition through the self-sealing membrane is highly consistent. In prior art systems which rely on one dip of the pin into the well to put down many spots, larger variances in the spot size tend to occur as the pin becomes dry through evaporation and deposition.

The well plate may also be provided with a self-sealing upper membrane, thereby fully enclosing the liquid in the well. The pin then pierces first through the upper membrane and then on through the liquid and the lower membrane. When the pin is withdrawn, the upper membrane self seals in the same manner as the lower membrane. Consequently, loss of sample from the wells by evaporation is prevented. This is especially useful for valuable or toxic samples and has the further advantage of greatly reducing the risk of sample contamination. Additionally, the upper membrane wipes the shank of the pin as it is withdrawn. This cleaning action cleans the pin while at the same time reducing loss of sample liquid. Moreover, the upper membrane ensures that accidental dropping of the well plate will not result in spillage.

Well plates may be provided in a variety of sizes and configurations. Standard 96, 384 or 1536 geometries may be provided. Specially sized well plates may also be developed to suit specific applications, or as a proprietary measure.

According to a second aspect of the invention, there is provided a head apparatus for operation with the multi-well plate of the first aspect of the invention. The head apparatus comprises a pin head and a mounting frame adapted to hold a multiwell plate beneath the pin head. A motor stage is operable to drive the pins of the pin head down through the multiwell plate. The pins can thus be actuated through the wells and through the self-sealing membrane to deposit a sample directly onto a spotting surface held below the head apparatus. The pin head and a well plate held thereto can thus be moved around together by a robotic guidance system, instead of moving the head independently of the well plate as in the prior art.

The pins are preferably fixed in the body portion so that their tips lie in a common plane distal the body portion. Slidably mounted pins are not necessary, resulting in a considerable cost saving.

Alternatively the pins may be individually actuatable and addressable, for example using conventional pin array addressing mechanisms.

Advantageously, the head may further comprise an abutment arranged to stop the pin tips being advanced beyond a plane defined by the abutment. The abutment is designed to contact the spotting surface simultaneously with the pins for spotting. The abutment thus defines the maximum travel of the pins during spot deposition. The pins are preferably constrained so that they either stand off slightly from the spotting surface or only just contact it at their points of maximum travel.

BRIEF DESCRIPTION OF THE DRAWINGS

For a better understanding of the invention and to show how the same may be carried into effect reference is now made by way of example to the accompanying drawings in which.

DETAILED DESCRIPTION

Figure 1A:
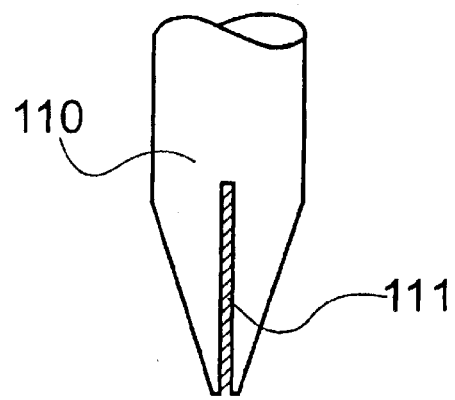
FIG. 1A is a schematic section of a split pin of the prior art.
Figure 1B:
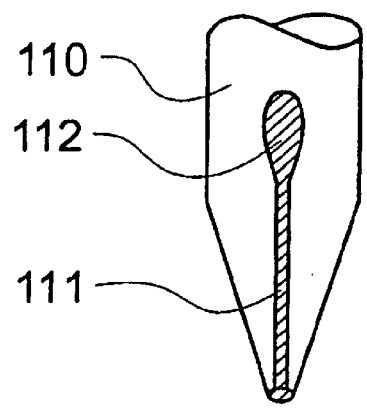
FIG. 1B is a schematic section of another split pin of the prior art.
Figure 2A:
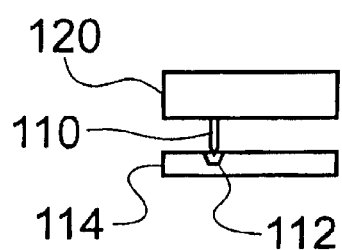
FIG. 2A shows sample collection by a pin from a well of a multi-well plate according to the prior art.
Figure 2B:
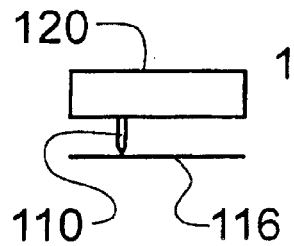
FIG. 2B shows sample deposition from a pin onto a microscope slide according to the prior art.
Figure 2C:
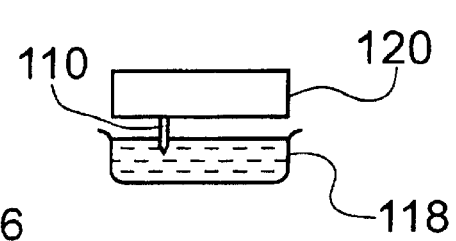
FIG. 2C shows pin washing according to the prior art.
Figure 3:
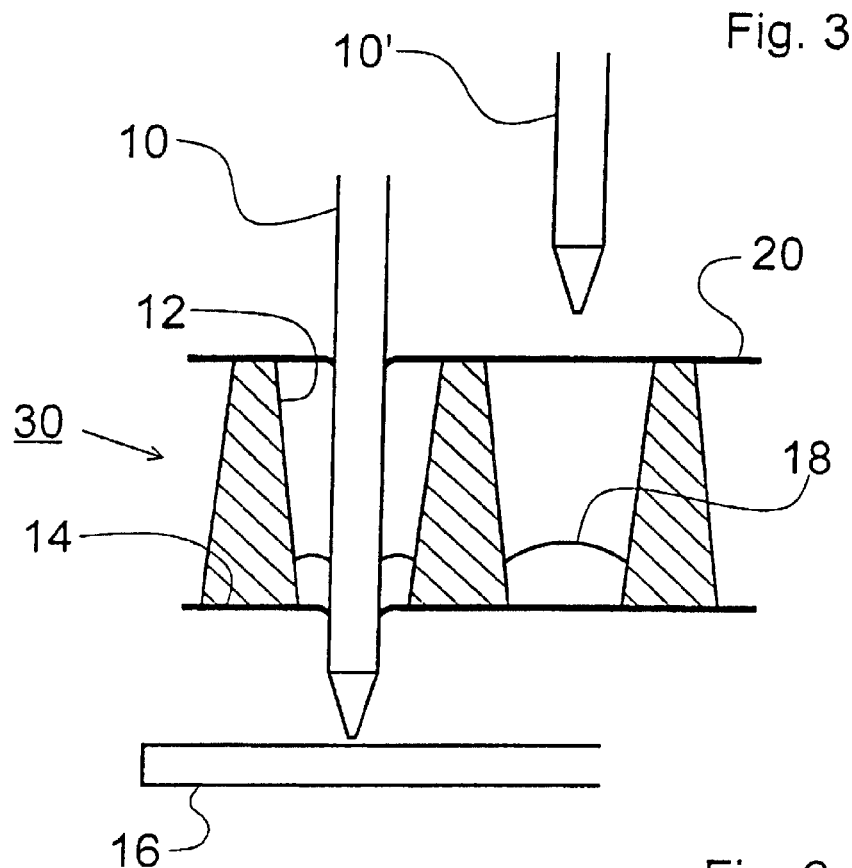
FIG. 3 is a schematic section through a part of a multi-well plate according to an embodiment of the invention with two pins and a slide also being shown.

FIG. 3 is a schematic drawing a section of part of a multi-well plate 30 according to an embodiment of the invention. Two pins 10 and 10', in two different operating positions, and a spotting surface 16 are also shown. The multi-well plate 30 comprises a plurality of wells, two of which are shown in FIG. 3. Each well is partially defined by a side wall 12 of generally frusto-conical shape defined in a main body of the well plate. The shape of the sidewall is not critical. The main body is made of conventional material. The main body has an underside to which is secured a lower membrane 14, and an upper side to which is secured an upper membrane 20. The lower membrane 14 defines a base to the wells. The upper membrane 20 defines a lid to the wells. The meniscus of a quantity of sample is shown with the reference numeral 18. In a concrete example, the meniscus position shown may represent about 5 microliters of sample liquid in each well, each well having a total volume of about 30 microliters. As well as sealing the well against spillage, the upper membrane 20 has the function of preventing sample loss through evaporation, which is important for precious, volatile or hazardous samples. The upper and lower membranes are made of self-sealing material, in other words material that automatically reseals after piercing with a pin or needle. The material use was obtained from USA/Scientific Plastics (Europe) Limited. This material has an adhesive backing, the adhesive being inert medical grade. Material such as rubber, silicone or PTFE may also be suitable for the membranes. Other, flexible, resilient materials may also be suitable.

In operation, to dispense an amount of sample, a pin is driven down from the position shown in pin 10'. The pin travels down through the upper membrane 20, then through the sample liquid and on through the lower membrane 14 until in close proximity with an upper surface of the spotting surface 16. The position is shown by pin 10 in FIG. 3. The liquid sample collected on the tip during its passage through the well is then deposited onto the spotting surface.

Experiments have shown that the quantity of sample carried through the membrane is highly consistent, providing spots of 80 micrometer diameter on a glass spotting surface, with very low variance. Spot size can be varied by using pins with varying tip diameters. In the experiments, the tips were not pressed against the spotting surface, but rather brought into a nominally zero stand-off or offset with the spotting surface using an abutment arrangement described further below. Liquid deposition is thus driven by surface tension and fluid flow effects, or by throwing the liquid off the tip by deceleration. In the experiments, the pins were traditional surgical needles made of 316 grade stainless steel modified by flattening the needle tips to a diameter of 50 micrometers. In the experiments, the lower membrane resealed, apparently perfectly, with no compromise to the sealing properties over a test with 1000 piercing actions in a single piercing position. No loss of sample (other than through the spot deposition) or damage to the membrane was detectable.

Other needle tip shapes and dimensions may be used to provide dosage control of the amount of deposited liquid. For example, fluted needle tips may be used.

Figure 4:
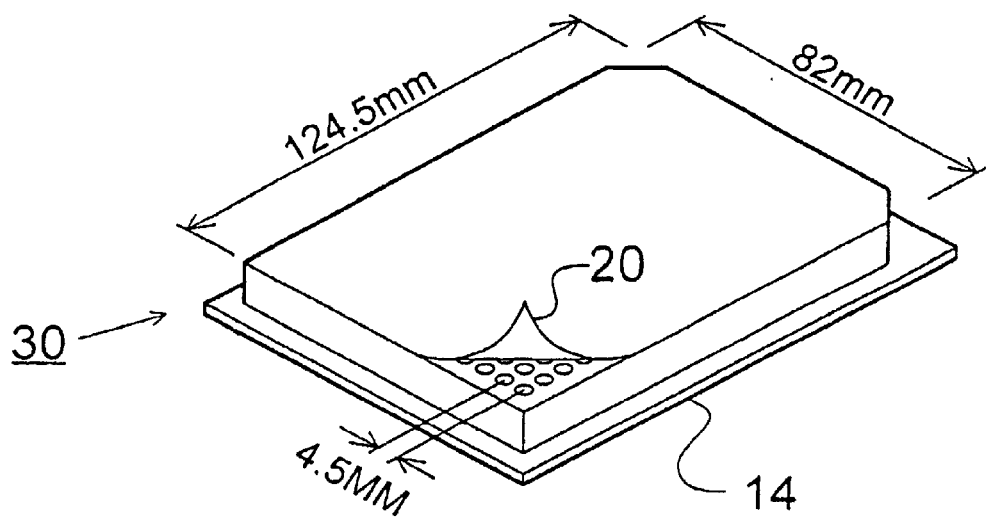
FIG. 4 is a schematic elevation of one example of a multi-well plate according to the embodiment of FIG. 3.

FIG. 4 shows an elevation of whole multi-well plate 30, a corner of the upper membrane 20 being peeled away for ease of viewing. The lower membrane 14 is also visible. The well plate conforms to the industry standard dimensions for a 384 well plate. Accordingly, the wells are arranged in a 4.5 mm square grid and the well plate is generally rectangular with outer dimensions of 124.5 mm by 82 mm to accommodate an array of 16 by 24 wells.

Although the membranes are shown as single sheets adhesively bonded to the well plate main body, it will be understood that the upper or lower membranes may be segmented. For example, individual membrane sections could be provided for each well or for groups of wells. Further, the membranes could be mechanically clamped onto the surfaces of the well plate main body, for example by a plate perforated with a grid of holes. Moreover, it will be understood that the upper membrane is optional. The upper membrane could be dispensed with altogether. Alternatively, the upper membrane could be fitted initially, after filling the well plate with sample liquid, to prevent evaporation and spillage during transport and storage. The upper membrane could then be removed immediately prior to microarraying. It will thus be understood that the upper membrane need not be a self-sealing membrane in all cases.

Figure 5:
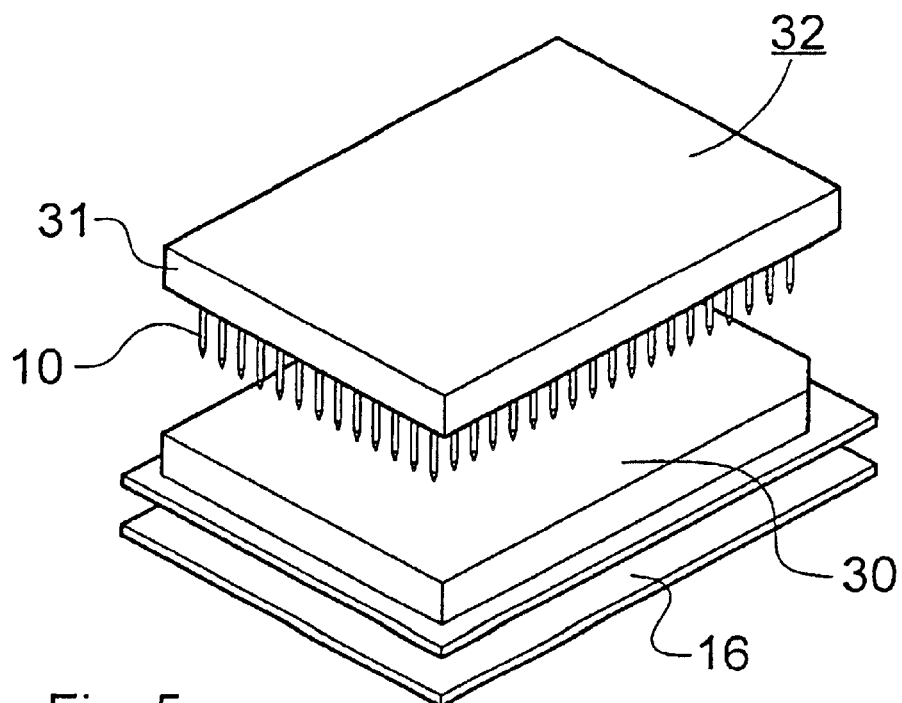
FIG. 5 shows a multi-well plate with pin head above and spotting surface below, in an operational configuration.

FIG. 5 shows another elevation view. The multi-well plate of FIG. 4 is shown again, together with a head 32 arranged thereabove and a non-standard slide 16 thereunder. The head 32 has 384 pins (actually needles as described above)

arranged in conformity with the well array of the multi-well plate, i.e. in a 16 by 24 array having a 4.5 mm grid.

Contrary to conventional designs, the pins 10 are fixed in a body part 31 of the head in order to allow them to be pushed through one or more membranes, as is required with the multiwell plates described herein. Fixing the pins is a great advantage since it would be very costly to build a head with 384 gravity located pins for a conventional multiwell plate. The small mass of the pins makes them sensitive to variations in the fit of the pins in their guide holes. As the number of pins is increased, it becomes increasingly difficult to avoid some pins falling freely and other pins sticking in their holes. Adding pin biasing springs has been proposed to overcome this problem, but this is not ideal since it increases impact forces on the pin tips, thereby increasing pin damage and wear rates. In any case, the biasing would have to be heavy if the pins were to be able to penetrate one or membranes.

Figure 6:
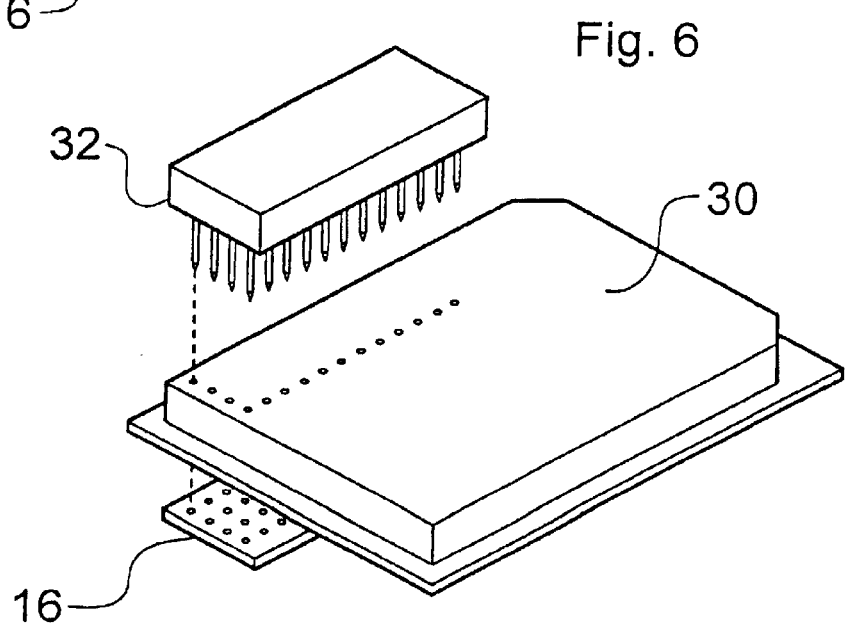
FIG. 6 shows a multi-well plate with an alternative pin head above and microscope slide below, in an operational configuration.

FIG. 6 is comparable to FIG. 5, but shows a smaller 48-pin head (reference numeral 32) with the pins arranged in a 4 by 12 array, again in a 4.5 mm square grid. Arranged under the 384 well plate 30 there is an industry standard microscope slide 16.

Figure 7:
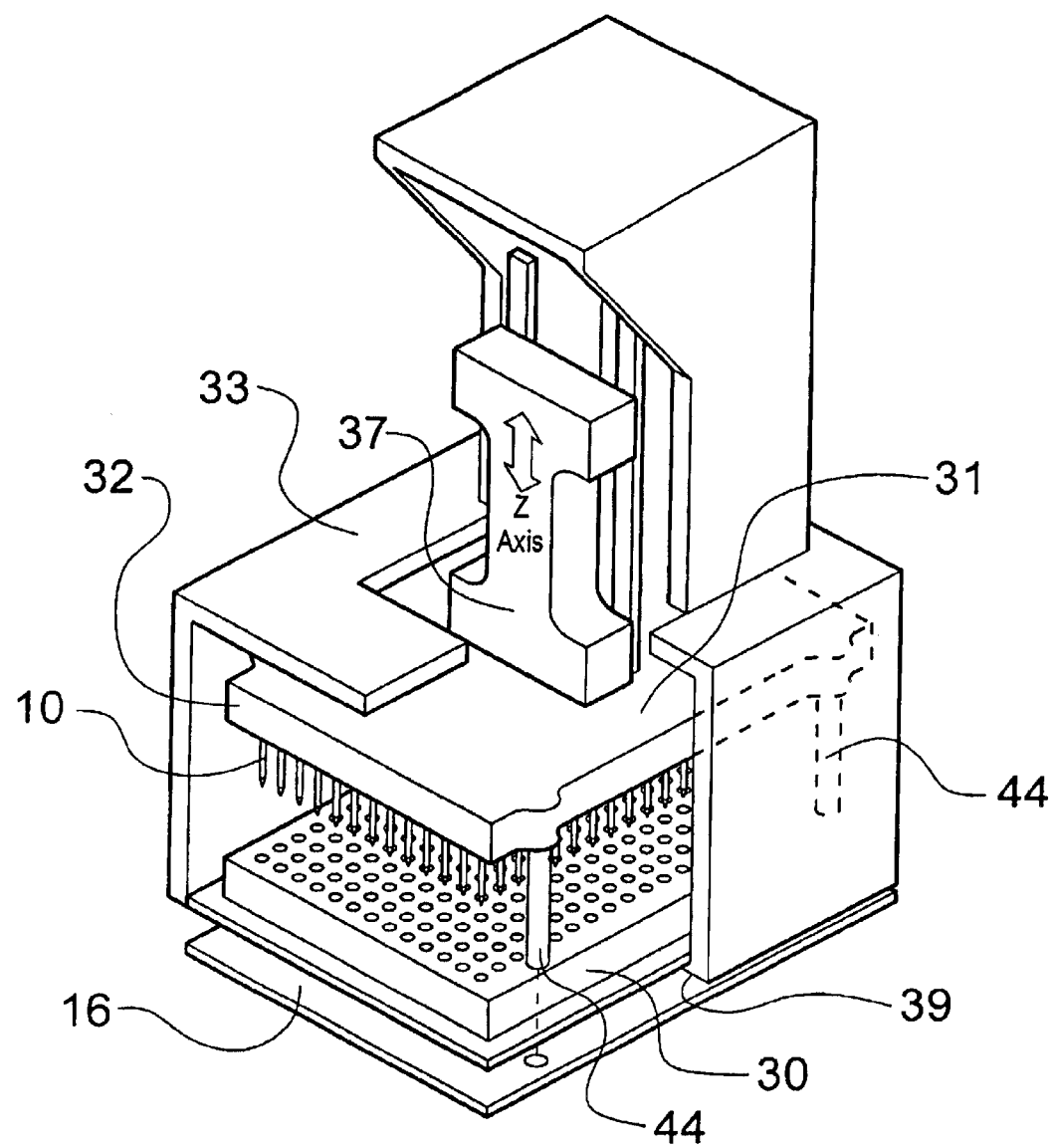
FIG. 7 shows in elevation a pin head with spotting surface and multi-well plate.

FIG. 7 is an illustration of a pin head 32 with ancillary mounting frame 33 and motor stage 37. The head 32 comprises a body portion 31 and an array of pins 10 extending down. The mounting frame 33 has a lower lip 39 for receiving and holding a multiwell plate 30 from an autofeed system (described further below). Any suitable guide, slot or retaining means could be used. The head 32 is held in the mounting frame 33 by the motor stage 37 which comprises a linear motor that is drivable to move the head up and down in the z-axis as illustrated. The body portion 31 of the head 32 has four pillars 44 serving collectively as an abutment. The pillars 44 are secured to the body portion 31 and extend down to terminate in a plane arranged approximately at or slightly below the common plane of the tips. The abutment extensions 44 from the head body portion 31 stop the pins at a fixed position just above or at the upper surface of the slide 16 so that liquid can pass from the pins to the spotting surface by fluid flow.

In use, the z-axis linear motor drives the body 31 down within the mounting frame 33 so that the pins 10 fixed in the body 31 pass through the wells of well plate 30 until the abutment 44 touches the spotting surface 16 whereupon the liquid is transferred.

Figure 8:
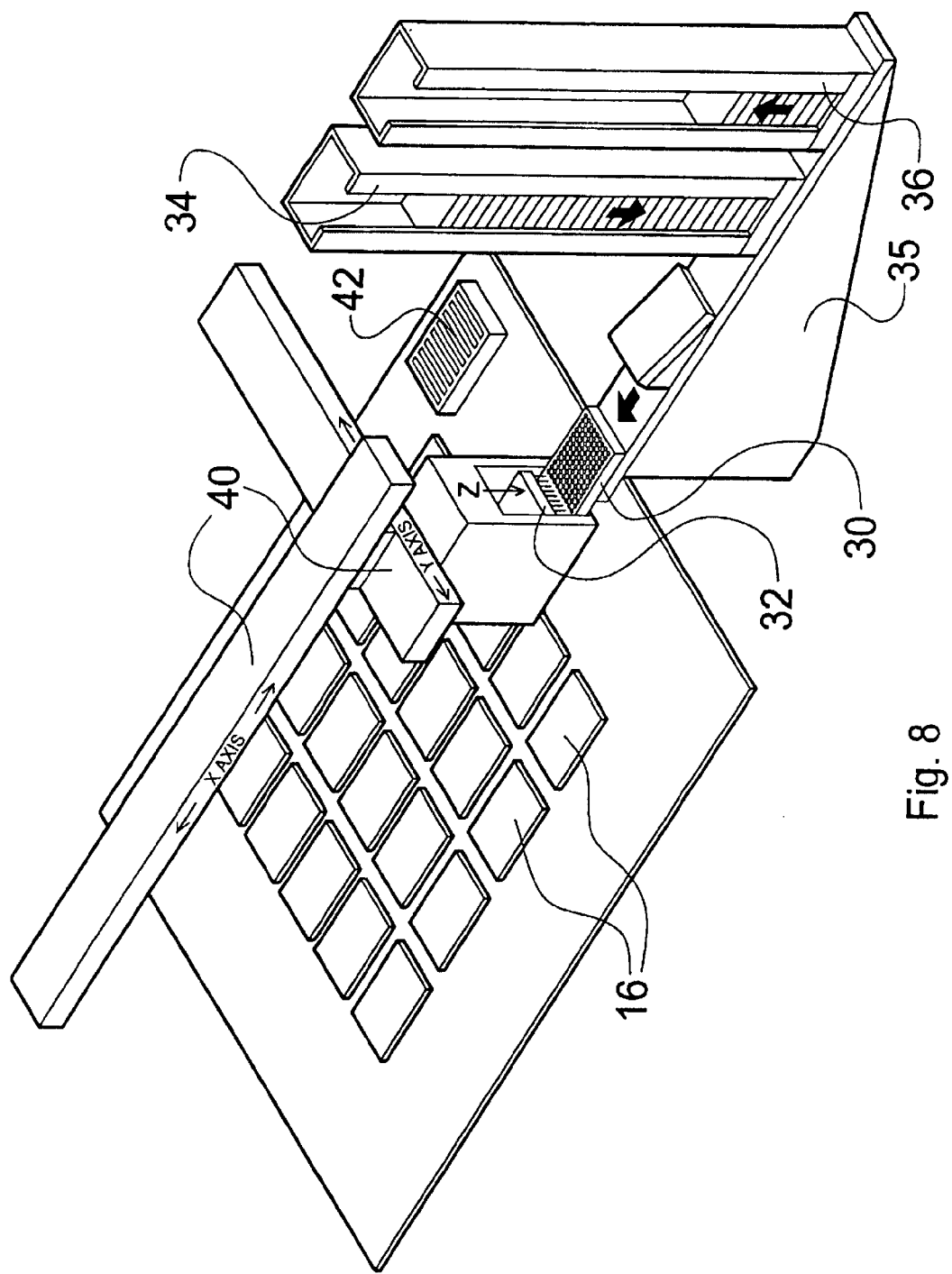
FIG. 8 is a schematic diagram of an automated spotting apparatus according to an embodiment of the invention.

FIG. 8 shows an automated microarraying apparatus according to an embodiment of the invention. A pin head 32 is held by a robotic xyz guidance system 40. An autofeed stacking system 35 is operable to load well plates 30 into the head 32 from a stack 34 of well plates. The autofeed stacking system 35 is also operable to restack well plates after use in another stack 36. The stack and restack processes may automatically remove and replace lids from the well plates, as is known from the prior art. Lids may be provided instead of or in addition to an upper membrane. A number of non-standard slides 16 are also shown. The slides are non-standard in that they are over-dimensioned by the provision of a margin region extending beyond the dimensions of a conventional slide. The xyz guidance system 40 is operable to position the head and well plate above any of the slides 16 for spotting. A wash station 42 is also shown which is provided for cleaning the head 32 after unloading a well plate into the restack stack 36.

It will be appreciated that although particular embodiments of the invention have been described, many modifications/additions and/or substitutions may be made within the spirit and scope of the present invention.

What is claimed is:

1. A method of dispensing liquid, comprising:
   (a) providing a reservoir of liquid bounded at least partially by a self-sealing membrane;
   (b) moving a tip of an elongated member through the liquid and then on to perferate the self-sealing membrane to release an amount of the liquid through the membrane;
   (c) withdrawing the tip to allow the self-sealing membrane to re-seal; and
   (d) again perforating the self-sealing membrane to release a further amount of the liquid through the membrane.

2. A method according to claim 1, wherein the self-sealing membrane is perforated by piercing with the elongate member and is allowed to re-seal by withdrawing the elongate member from the self-sealing membrane.

3. A method according to claim 2, wherein perforation occurs by moving the tip of the elongate member through the liquid of the reservoir into contact with and then through the self-sealing membrane, the elongate member then being withdrawn from the liquid.

4. A method according to claim 1, wherein a further self-sealing membrane is provided above the reservoir to inhibit loss of material from the liquid by evaporation during dispensing.

5. A method according to claim 1, wherein the reservoir of liquid is with a well plate comprising:
   an upper surface;
   a lower surface;
   an array of wells extending between the upper surface and the lower surface;
   a lower membrane extending over the lower surface to form a self-sealing, liquid-tight base for the wells.

6. A method according to claim 5, wherein the lower membrane is formed of a single sheet of material.

7. A method according to claim 5, wherein the lower membrane is formed of multiple sheets.

8. A method according to claim 7, wherein there is one sheet for each of the wells.

9. A method according to claim 5, further comprising an upper membrane extending over the upper surface to form a top for the wells.

10. A method according to claim 9, wherein the upper membrane is made of self-sealing material.

11. A method according to claim 5, further comprising a removable cover extending over the upper surface to form a top for the well plate.

12. A method according to claim 5, wherein the array of wells conforms to a square grid having a grid spacing of one of: 2.25 and 4.5 millimeters.

13. A method according to claim 5, wherein the array of wells has one of: 96, 384 and 1536 wells.

14. A method according to claim 1, wherein a head apparatus for microarraying multiwell plates is used, the head apparatus for microarraying the multiwell plate comprising:
   a pin head having an array of pins;
   a mounting frame adapted to hold a multiwell plate beneath the pin head; and
   a motor stage operable to drive the array of pins down through the multiwell plate held in the mounting frame to deposit a sample onto a spotting surface below the head apparatus.

15. A method according to claim 14, wherein the pin head further comprises:

a body portion to which the pins are fixed so that their tips lie in a common plane distal the body portion.

16. A method according to claim 14, wherein the pin head further comprises:

an abutment extension extending down from the body portion to terminate in a further plane arranged approximately at or below the common plane of the tips.

17. A method according to claim 14, wherein the pins are individually drivable.

18. A method according to claim 14, the head apparatus further comprising:

a robotic guidance system operable to load and unload multiwell plates into the mounting frame.

19. A method of according to claim 14 further comprising:

providing a multiwell plate in the mounting frame; and driving the array of pins of the pin head down through the multiwell plate to deposit a sample onto a spotting surface below the head apparatus.

* * * * *